United States Patent [19]

Fischer et al.

[11] Patent Number: 5,480,373
[45] Date of Patent: Jan. 2, 1996

[54] DEVICE FOR TRANSPORTING IONS, IN PARTICULAR, PROTONS

[75] Inventors: Gerhard Fischer, Vaduz, Liechtenstein; Ulrich Warnke, Scheidt; Herbert König, München, both of Germany

[73] Assignee: Dr. Fischer Aktiengesellschaft, Vaduz, Liechtenstein

[21] Appl. No.: 178,305

[22] PCT Filed: Jul. 3, 1992

[86] PCT No.: PCT/DE92/00564

§ 371 Date: Jan. 7, 1994

§ 102(e) Date: Jan. 7, 1994

[87] PCT Pub. No.: WO93/00960

PCT Pub. Date: Jan. 21, 1993

[30] Foreign Application Priority Data

Jul. 9, 1991 [DE] Germany ............. 41 22 718.2

[51] Int. Cl.⁶ .................................... A61N 1/00
[52] U.S. Cl. ................................................ 600/14
[58] Field of Search ............... 600/9–15; 604/20; 435/173

[56] References Cited

U.S. PATENT DOCUMENTS

| | | |
|---|---|---|
| 2,558,270 | 6/1951 | Reiter ............................ 600/14 |
| 3,566,877 | 3/1971 | Smith et al. . |
| 4,428,366 | 1/1984 | Findl et al. . |
| 4,641,633 | 2/1987 | Delgado . |
| 4,654,574 | 3/1987 | Thaler . |
| 4,818,697 | 4/1989 | Liboff et al. . |
| 5,224,922 | 7/1993 | Kurtz .............................. 600/13 |

FOREIGN PATENT DOCUMENTS

| | | |
|---|---|---|
| 0136530 | 4/1985 | European Pat. Off. . |
| 0152963 | 8/1985 | European Pat. Off. . |
| 0266907 | 5/1988 | European Pat. Off. . |
| 0377284 | 7/1990 | European Pat. Off. . |
| 2707574 | 8/1978 | Germany . |
| 3244582 | 12/1984 | Germany . |
| 3335018 | 4/1985 | Germany . |
| 3828043 | 5/1989 | Germany . |
| 675970 | 11/1990 | Switzerland . |
| 2242362 | 10/1991 | United Kingdom .............. 600/15 |

Primary Examiner—Angela D. Sykes
Assistant Examiner—Samuel Gilbert
Attorney, Agent, or Firm—Robert W. Becker & Associates

[57] ABSTRACT

A device has a generator for generating low-frequency pulsed electric currents and a transmitter coil connected to the generator for applying electromagnetic fields to a body region of a living organism and is designed for transporting ions from intra-corporal electrolyte liquids of the living organism into and through surrounding vessel walls and membranes such that the transmitting energy is selected to such a high value that the energy induced within the electrolyte liquid is greater than a thermal energy and is within a cell-specific amplitude window. Pulsed currents generated within the transmitter coil by the generator have the following properties: a) a basic current pulse of a first duration consists of a square current and a superimposed current increasing according to an exponential function; b a pulse interval subsequent to the basic current pulse having a second duration that is at least equal to the first duration; c) a basic frequency of the basic current pulse with the pulse interval is 100 to 1000 Hz; d) an amplitude of a sequence of the basic current pulses is modulated with a frequency of 0.5 to 35 Hz to yield a modulation amplitude; e) the sequence of the basic current pulse is emitted as a series for a period of 0.3 to 1.0 sec; and f) the series is followed by a series interval of 0.7 to 5.0 sec.

25 Claims, 5 Drawing Sheets

DEVICE FOR TRANSPORTING IONS, IN PARTICULAR, PROTONS

BACKGROUND OF THE INVENTION

The present invention concerns a device having a generator for producing low-frequency pulsed electrical currents and a transmitter coil connected to the generator, whereby the electromagnetic fields generated by the transmitter coil are used for applying pulses to an area of the body requiring treatment.

Devices of this kind are generally known from the literature and also from patent documents. For example, U.S. Pat. No. 4,428,366 describes an electromagnetic apparatus and method for reducing the glucose level in blood serum using unipolar pulsed magnetic fields with a low pulse sequence frequency of between 5 and 75 Hz and an individual pulse duration of, for example, 350 microseconds. In this example, each individual pulse has a pulse tilt in order to guarantee a constant magnetic field for the whole duration of the individual pulse. This is monitored by means of a display which receives information from a measuring coil installed within the area of irradiation.

U.S. Pat. No. 4,641,633 A1 deals with an electronic system for activating, influencing and/or modifying the development of cells, organs and the entire organism of living individuals. In accordance with this publication, unipolar square-wave pulses are used, which have a considerable edge steepness and a pulse sequence frequency between 1 and 120 Hz, and are applied to the area to be irradiated by means of an antenna. In this instance, a high frequency oscillation keying is superimposed over the individual pulses, whereby the oscillation frequency should be in the region of between 10 kHz and 100 MHz.

European publication 0 152 963 A2 describes an electrotherapeutical device which involves electrodes attached to the area of the body to be treated via which low frequency pulsed electrical oscillations are fed to the body tissue in order to generate electromagnetic fields. The device operates essentially in accordance with the Joule effect on tissue in combination with an alternating electromagnetic field.

German Patent 1 38 28 043 A1 describes a device for medical treatment for influencing the magnetic-energetic processes in living human or animal organisms, whereby the device has one or more inductance coils inside a flat, flexible pad which are operated by pulsating DC current. The pulsating DC current generates a low frequency pulsating magnetic field with a frequency between 15 and 20 Hz, for example.

European publication 0 266 907 A2 discloses an apparatus for irradiating a patient's body, in which apparatus a high frequency oscillation of, for example, 27 MHz is pulsed at a low frequency. The pulse frequency should be between 1 Hz and 10 kHz with an individual pulse duration between approximately 10 and 100 microseconds.

Finally, Swiss patent 675 970 A5 describes a device for treating living organisms using an intermittent, pulsating constant magnetic field. Pulse packages consisting of several individual pulses are emitted, whereby the amplitudes of the pulses in each pulse package may be constant, rising, falling or rising and falling.

All these devices and methods have in common that they are designed to influence biological processes by heating and/or electromagnetic irradiation.

Additionally, it is known that receptors referred to as baroreceptors are located in blood vessels in the region of the coronary circulation and the neck which baroreceptors assist the body in controlling blood pressure, and that it is possible to influence these baroreceptors using electromagnetic fields so that the blood circulatory system is activated. In this manner, it was also possible to widen the capillaries, thus leading to improved blood flow to the corresponding areas of the body. Baroreceptors are only located at certain points in the blood vessels, and, consequently, the possibilities of influencing them are somewhat limited.

As a result, an improvement in the supply to and drainage from certain vessels and areas of the body is only indirectly achieved due to a general improvement in the blood flow. It is not possible to influence the lymphatic system at all because it does not contain any baroreceptors.

In contrast to these examples, the purpose of the invention is to provide a device for transporting ions, in particular, protons in order to make possible a targeted effect of the ion concentrations in any area of the body of humans and animals as required.

SUMMARY OF THE INVENTION

In accordance with the present invention, this task is fulfilled by a device as described in the introduction by selecting the level of transmission energy high enough so that the energy induced in the electrolytic fluid is greater than the thermal energy and lies within the limiting values referred to as the cell-specific amplitude window, and by the fact that the pulsed currents produced by the generator in the preferably low induction transmitter coil have the following characteristics:

- the basic current pulse consists of a square wave current superimposed on a current which rises approximately according to an exponential function, followed by a pulse interval of at least the same duration,
- the basic frequency of the basic current pulses with basic pulse intervals is between 100 to 1000 Hz, and preferably 200 Hz,
- the amplitude of the basic pulse sequence is modulated with a modulation frequency of between 0.5 to 25 Hz, preferably 20 Hz, in its amplitude,
- the modulated basic pulse sequence is transmitted as a series of pulse sequences for a duration of 0.3 to 1.0 seconds, with each transmission being followed by a pulse series interval of between 0.7 and 5.0 seconds.

The inventive device is primarily characterized by:

a generator for generating low-frequency pulsed electric currents;

a transmitter coil connected to the generator for applying electromagnetic fields to a body region of a living organism;

the device designed for transporting ions from intracorporal electrolyte liquids of the living organism into and through surrounding vessel walls and membranes such that a transmitting energy is selected to such a high value that the energy induced within the electrolyte liquid is greater than a thermal energy and is within a cell-specific amplitude window; and wherein pulsed currents generated within the transmitter coil by the generator have the following properties:

a) a basic current pulse of a first duration consists of a square current and a superimposed current increasing according to an exponential function;

b) a pulse interval subsequent to the basic current pulse having a second duration that is at least equal to the first duration;

c) a basic frequency of the basic current pulse with the pulse interval id 100 to 1000 Hz;

d) an amplitude of a sequence of the basic current pulses is modulated with a modulation frequency of 0.5 to 35 Hz to yield a modulation amplitude;

e) the sequence of the basic current pulse is emitted as a series for a period of 0.3 to 1.0 sec; and f) the series is followed by a series interval of 0.7 to 5.0 sec.

The ions are preferably protons.

The transmitter coil preferably has low induction.

The basic frequency is preferably 200 Hz.

The modulation frequency is preferably 20 Hz.

Expediently, a ratio of the first duration to the second duration is substantially 2:3.

Advantageously, high frequency pulses of a 10 to 100 kHz are superimposed over each the basic current pulse.

The modulation amplitude preferably forms substantially an isosceles triangle.

The sequence of the basic current pulses is advantageously modulated without a polarity reversal.

In a preferred embodiment, the device further comprises a measuring coil, wherein during the series interval a substantially sinusoidal measuring current of a frequency in a range of 100 kHz is supplied to the transmitter coil, and wherein a measured signal of the measuring coil is used for determining an electric impedance and electric polarization of the body region being irradiated.

The generator advantageously further comprises a bio-feedback control system for adjusting optimal field parameters.

The generator preferably has an adjustable frequency, adjustable amplitude, adjustable curve shape, and adjustable on- and off-times.

The bio-feedback control system may comprise a blood pressure measuring device, a thermograph, a pulse measuring device, a breathing volume measuring device for determining control parameters.

The bio-feedback control system comprises a measuring coil for measuring a magnetic field reflected by the living organism being irradiated.

The device preferably further comprises an evaluation circuit connected to the measuring device, the evaluation circuit further comprising a regulator, wherein an evaluated signal of the evaluation circuit is used to optimize the parameters of the transmitter coil pulses via the regulator.

The measuring coil is preferably circular and has a diameter of 20 cm, and wherein the transmitting energy is selected to such a value that the magnetic field reflected by the living organism generates in the measuring coil a measuring voltage of 20 to 30 mV.

Preferably, three the measuring coils 42–44 are provided that are switchable, wherein each the measuring coil has a diameter adapted to a body region to be treated.

The transmitter coil is expediently designed such that local field peaks of the field emitted onto the living organism are prevented.

Advantageously, windings of the transmitter coil are forming a quadrupole.

The best known intra-bodily electrolytic fluids in humans and animals are blood and lymph. In the body, blood is the universal means of transportation for oxygen, carbon dioxide, water, salts and other electrolytes, nutrients, metabolic products, heat, catalytic substances such as hormones and enzymes, antibodies, substances for healing wounds, etc. Based on its flow characteristics, blood is not a Newtonian fluid and has more similarities to an emulsion than to a suspension. Its pH value is approximately 7.38 and its relative dielectric constant is in the region of 80 due to the high water content, at least within the low frequency range. Lymph is a colorless to yellowish bodily fluid which derives from blood plasma and which enters tissue through the capillaries. Lymph surrounds all cells. It collects in cavities in tissue and in voids. The drainage takes place initially via narrow lymph capillaries that combine to larger lymph vessels. Before these vessels re-open into the blood system, they pass through the lymph nodes. Lymph provides nutrients to the tissue and transports metabolic products out of the tissue. Lymph contains approximately 95% water. As another important intrabodily fluid, one should mention the liquor which surrounds the brain and the spinal cord.

The so-called acid/base balance is particularly important for the correct function of human and animal organisms. This balance must be maintained at a constant level within narrow limits because otherwise serious disturbances of functions such as ion antagonism, oxygen transportation within the blood, cell membrane permeability in the tissue, enzyme properties, etc. may occur. The acid/base balance is described using the so-called Henderson-Hasselbach equation. The acid/base balance is closely linked to the general interbalance of electrolytic substances in the body.

Thanks to the combined effect of pulse frequency, pulse shape, pulse energy and the shape of the transmitter coil, it is possible to funnel ions, in particular protons, from the intra-bodily electrolytic fluid, for example the blood, lymph or liquor, in a targeted manner directly into the tissue walls and membranes which surround them. Under normal conditions, this effect is not possible because the lipids in the blood vessel membranes which are in contact with the blood carry a negative charge. The field resulting from this charge exceeds the thermal energy and extends approximately 1000 Å into the plasma. The concentration of cations near the surface of the vessel is higher than that in the plasma phase by approximately a factor of ten. This means the local pH value is lower than that in the electrolytic fluid by a factor of ten.

Under normal circumstances, the surface tension represents an electrical barrier which prevents protons and other ions from penetrating the vessel walls. The energy required to permit an ion with a radius of $10^{-10}$ m to pass from an aqueous to a liquid medium is approximately 22.6 eV. The surface tension of the vessel walls and membranes of the body varies extremely. This is taken into account by means of the amplitude modulation of the basic pulse sequences. In this connection, an effect referred to as the window effect has to be taken into consideration, namely that the induced voltages only enable ions and protons to penetrate the vessel wall if their amplitude lies within a cell-specific amplitude window. Amplitudes that are too low or too great prevent ion transport through vessel walls and membranes.

The existence of cell-specific amplitude windows has been known for many years, for example, from a publication by Adey in the journal "Proceedings of the IEEE", 68,1, 119–125, published in 1980 and from a publication by Basset in the journal "Orthopädie" 13, 64–77, in 1984.

An electric potential of a specific intensity and direction is induced in the electrolytic fluid under the influence of the inventive pulsating electromagnetic fields. Under the influence of these electromagnetic fields, the ions are moved towards the vessel walls, whereby protons due to their great mobility are preferably moved. The resulting interaction causes the induced field to be concentrated in a small area. This effect produces what is referred to as concentration polarization.

The selection of an exponential function (e-function) for the amplitude of the individual basic pulses results in the important consequence for the medicinal/biological effect that voltage pulses are induced that have a substantially identical shape and, most importantly, exhibit no phase shift relative to the current or field pulses. Only at the end of each basic current pulse a very brief voltage pulse of reversed polarity is induced; however, this disturbs the positive effect only to a minor degree. Due to the fact that the transmitted current pulses, or the magnetic field they generate, and the induced voltage pulses have the same shape and the same phase, the energy transmitted is of the maximum value. Additionally, a surprising effect is produced, namely that both the positive and negative ions in the electrolytic fluid move in the same direction. Usually, positive and negative ions move in opposite directions. With the inventive process it is thus possible to transport positive and negative ions from the electrolytic fluid of the body into the same cells simultaneously. The voltage induced in the vessel wall is increased as a result of the polarization potential. Due to the fact that the vessel walls, and, in particular, the membranes of the vessel walls, are very thin, fields of very considerable intensity are produced, even if the absolute value of the induced voltages remains relatively small. For example, a voltage of only 30 mV induced in a membrane 200 nm thick leads to a field intensity of 150 kV/m. It should be noted that field intensities of this magnitude can only be attained using inductive methods and magnetic fields, and by no means can be produced using capacitative or galvanic methods involving electrodes. Due to the high electric conductivity of the intra-bodily electrolytic fluids the vessels form essentially a Faraday cage, the interior of which remains free of electrical fields. However, inductive excitation makes use of the same electrical conductivity of the intra-bodily electrolytic fluids in order to generate potentials and fields.

The aforementioned negative charge of the vessel walls relative to the charge of the electrolytic fluids also results from the differences in the relative dielectric constants in the vessel walls on the one hand and the fluids on the other hand. Due to their high water content, blood and lymph have relative dielectric constants in the range of 80. The dielectric constant of the vessel walls is approximately 3 to 5. The voltages and currents or fields induced in the electrolytic fluids in accordance with the present invention are capable of neutralizing this potential threshold which is referred to as the zeta potential. As a consequence, it becomes possible for ions, and in particular, the mobile protons, to enter the cell and vessel walls to a greater degree. The enrichment of protons in the cell and vessel walls generates an inversely polarized potential threshold that prevents the protons and ions from leaving the cell and vessel walls again.

The change in proton concentration additionally favorably affects the pH value, especially in the region of the vessel walls.

All these effects are especially effective the thinner the thickness of the vessel walls is. Accordingly, they are especially strong in the areas around the arterial capillaries where, as is well known, the oxygen transported by the blood is exchanged for carbon dioxide given off by the cells.

In addition to the effects described above that have long-term benefits, the electromagnetic fields also have other effects. At this point, only the following features will be mentioned: electrostriction of membranes and vessel walls as a result of body-borne sound with actuation of mechanical and piezo-receptors; the alignment of polyvalent ion chains; the tangential displacement of adsorbed counter ions; the force effect on dielectric bodies in homogenous and inhomogeneous fields; and electro-osmosis.

The basic frequency of the basic current pulse is preferably adjusted to match the mechanical resonance of the blood and lymph vessels.

The optimum induced amplitude shape has been demonstrated as that of an isosceles triangle, whereby in a further embodiment of the present invention, the polarity of the amplitude does not change. Both special current curve forms and special transmitter coils are necessary in order to be able to induce such pulses. Advantageously, high frequency pulses of a frequency of approximately 10–100 kHz are superimposed on the basic pulses. This frequency is adjusted to match the capacitive transfer through the membranes.

In order to allow the effects introduced by the induced voltages and fields to function in the optimum manner, the organism requires certain pauses. Therefore, it is advantageous to switch the fundamental pulses on and off at regular intervals, whereby switch-on and switch-off times can be varied between 0.3 sec to 0.7 sec and 0.7 sec to 5.0 sec.

By adjusting the field parameters, optimal effects on the organism can be produced. Advantageously, this adjustment is controlled by using biofeedback.

For this purpose, according to a first variant, a blood pressure measuring gauge is connected to an inventive device. In this case, the control system adjusts to an optimum blood pressure level.

In accordance with a second variant, a thermograph is connected. In this case, the control system adjusts to optimal heating of the desired area of the body by means of improved circulation.

In accordance with a third variant, a pulse measuring device is connected. This is based on the recognition that, if the pulsed electromagnetic fields are set to have the optimal effect, the pulse rate slows.

In accordance with a fourth variant, a breathing volume measuring device is connected. This is based on the recognition that, if the pH value in the liquor is lowered, the breathing volume increases, e.g. the subject breathes more deeply.

However, external auxiliary apparatus can be dispensed with if, in accordance with the present invention, the transmitter coil, which is designed as a low-induction flexible flat coil, is combined with at least one inductive measuring coil. The latter must also have extremely low-inductance in order to be able to record the extremely weak fields induced in the organism with as little distortion as possible.

This measuring coil detects the magnetic field which is reflected and phase-shifted to a lesser or greater degree by the organism. The measured signal is evaluated by a suitable highly sensitive electronic evaluation circuit, whereby the parameters of the transmitted current pulses are optimized by means of a regulator which may optionally be built in.

It is not only the shape of the transmitter coil but also the shape of the measuring coil which are important in ensuring optimum function and effect of the electromagnetic fields within the organism. Surprisingly, it has been found that optimum effects in the organism are achieved when the transmitted current pulses are selected so strong so that a measuring voltage between 20 and 30 mV is induced in a circular measuring coil with only a single loop and a diameter of 20 cm. However, it must be ensured that the extent of the organism area influenced by the electromagnetic fields is also approximately 20 cm or more in diameter. If smaller bodily areas are to be measured, for example, arms or legs, a measuring coil of a correspondingly reduced size must be used. The resulting reduced measuring voltage of the system is then calibrated in the control circuit.

As far as the shape and the design of the transmitter coil is concerned, it has surprisingly been found that the best results can be achieved if the loops in the transmitter coil take the shape of an oval spiral and are distributed on both sides of the carrier plate.

Thanks to the extremely low-inductance design, the transmitter coil is capable of transmitting optimal pulse shapes, pulse frequencies, and pulse energies without any distortion.

In each case, the shape of the transmitter coil should be such that the required voltages and fields can be produced at the location of effect in the body being irradiated without generating any dangerous local peak field values. Pursuant to this, the optimal arrangement of the transmitter coil is that referred to as a quadrupole.

For the same purpose the carrier plate which carries the windings of the transmitter coil may be adapted to the profile of the part of the body to be treated.

BRIEF DESCRIPTION OF THE DRAWINGS

With the aid of the drawings the present invention will be explained in greater detail by means of various embodiments. It is shown in schematic representation, in.

DESCRIPTION OF PREFERRED EMBODIMENTS

Figure 1:
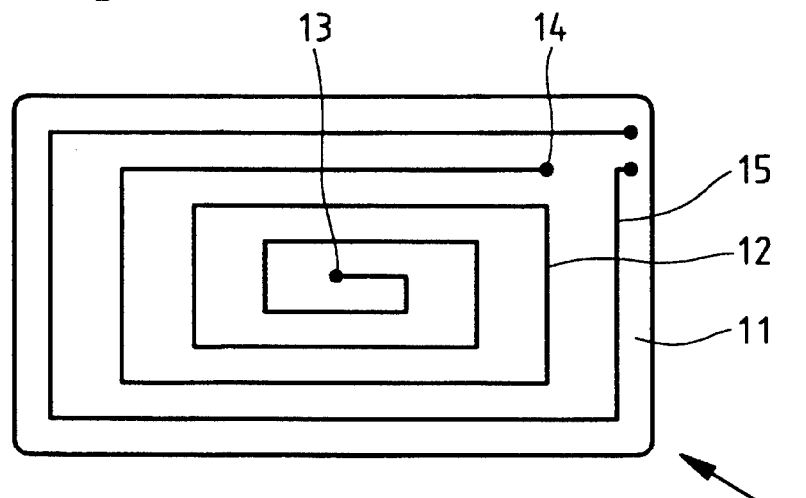
FIG. 1 a plan view of a first transmitter coil.

FIG. 1 shows a plan view of a first arrangement of a transmitter coil 10. The actual transmitter loop 12 is located on a carrier plate 11 made of highly flexible insulating material and takes the form of an oval spiral which for the sake of simplicity is shown in the drawing with a rectangular cross-section. The inner end 13 of the loop is through-contacted to another coil with the same winding direction located on the other side of the carrier plate 11. The current is supplied at the outer end of the loop 14.

An inductive measuring coil 15 is wrapped around the transmitter coil 12. This coil 15 picks up the reflected field which has been partially reduced in intensity and phase-shifted within the organism to be treated and sends it to a suitable electronic circuit. Suitable highly-sensitive electronic circuits are known, for example, in the form of in-phase equipment.

Figure 2:
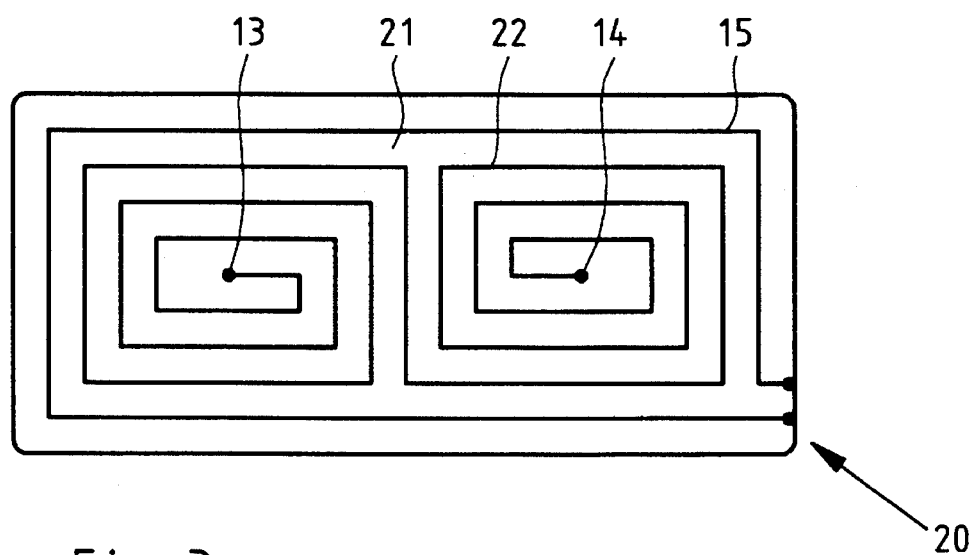
FIG. 2 a plan view of a transmitter coil in the form of a quadrupole.

FIG. 2 shows a second arrangement of a transmitter coil 20. Two oval spirals 22 with opposite winding directions are located on the carrier plate 21. Corresponding loops are located on the other side of the carrier plate 21. This special loop arrangement produces an effect known as a quadrupole, the field lines of which are even better suited to produce the required effects in the organism. In this case, too, a measuring loop 15 is provided.

Figure 3:
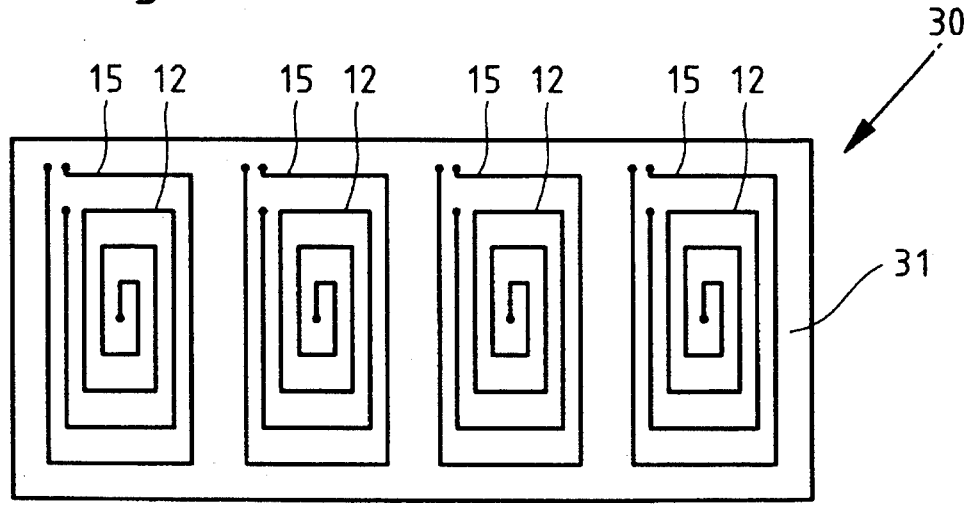
FIG. 3 a plan view of a multiple coil.

FIG. 3 shows a third arrangement of a transmitter coil 30 which is especially intended for use in clinical practice. In the present invention, four transmitter coils 12 with an appropriate measuring coil 15 are fitted on a carrier 31 which is once again highly flexible and the size of which can correspond approximately to the size of a bed cover. By means of switching the individual transmitter coils on and off, it is possible to treat different bodily sections of varying sizes at the same time. A cover protects the carrier from damage and soiling.

Figure 4:
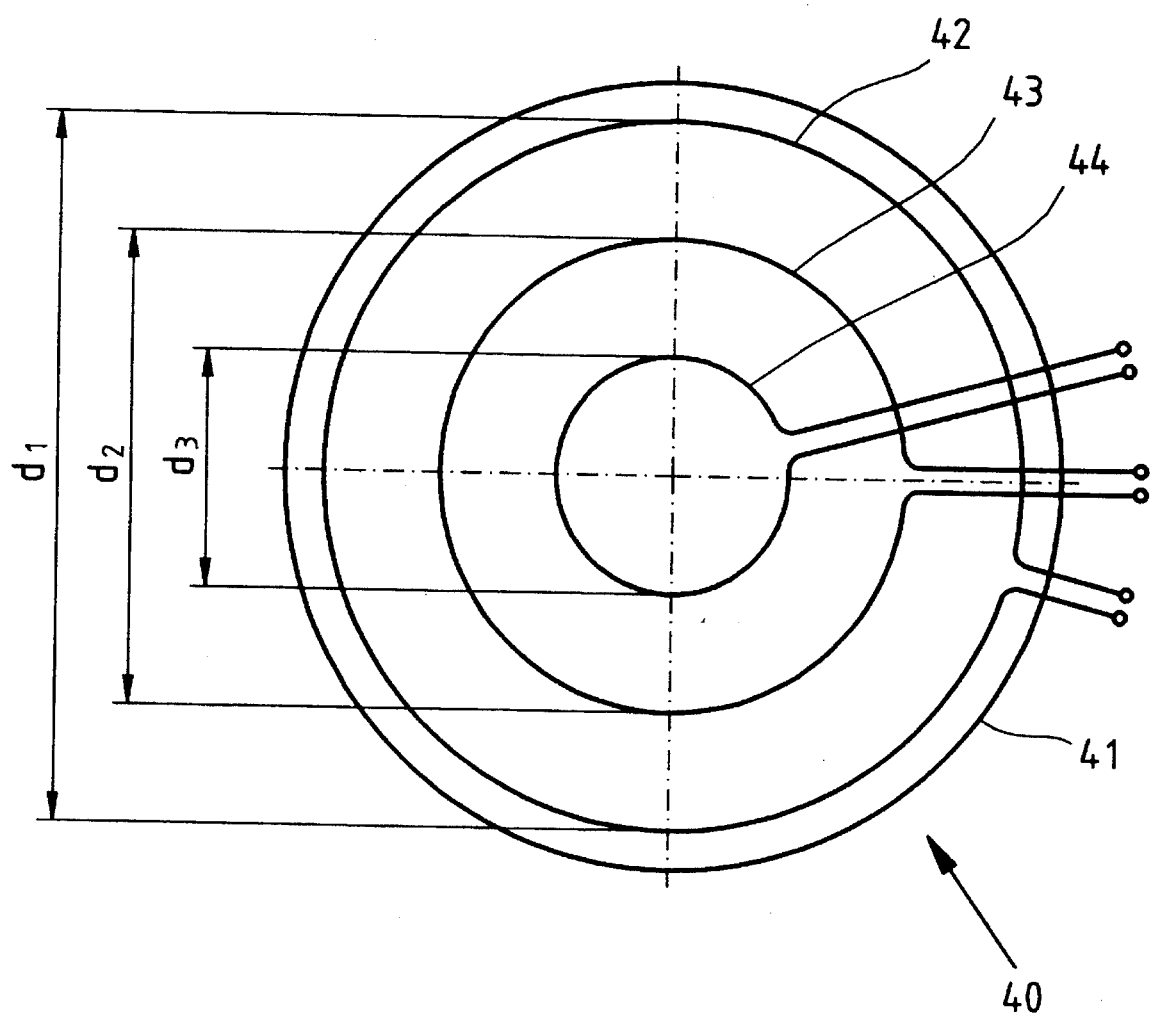
FIG. 4 a plan view of a multiple measurement coil.

FIG. 4 is intended to deal with an interesting and fundamental aspect of the present invention.

The drawing shows a transmitter coil 40 with a flexible carrier 41, in which, however, the spiral loops of the transmitter coil 40 are not illustrated. The figure depicts three measuring coils 42, 43, 44 with varying diameters $d_1$, $d_2$ and $d_3$. Tests have been conducted which show that the effect of the pulsed electromagnetic fields on the organism are at their optimal level if a voltage of 20 to 30 mV is induced in a circular measuring coil with only a single loop and a diameter of 20 cm, providing that the area of the body being irradiated is correspondingly large. If larger areas of the body are to be treated, an insufficiently dimensioned measuring coil would only pick up a portion of the reflected energy and thus produce the erroneous impression that the transmitter energy was not adequate. For this reason, measuring coils of different diameters are used in practice, whereby the differing induction voltages which then arise as a result of the system configuration are calibrated in the connected measuring apparatus.

Figure 5:
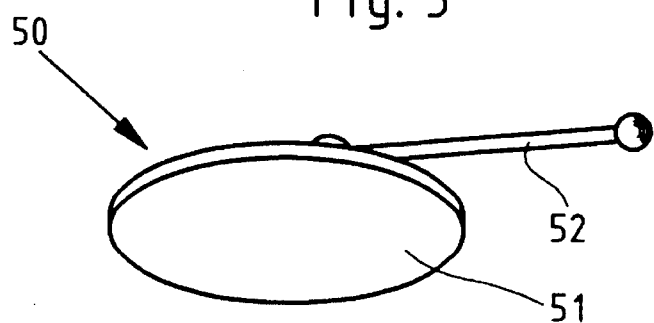
FIG. 5 a transmitter coil arrangement for treating parts of the body with large surface areas, FIG. 6 a transmitter coil arrangement for treating arms and legs, FIG. 7 the design of this transmitter coil in an exploded view, FIG. 8 an optimal basic current pulse with corresponding basic pulse separation, FIG. 9 an induced pulse shape plotted as a voltage/time graph FIG. 10 the basic pulse in FIG. 8 using a different time scale and featuring amplitude modulation, and FIG. 11 the pulse sequence series featuring different time scale, and FIGS. 12 to 14 circuit details of the base unit, not depicted in detail in FIG. 5, as well as showing adjustment circuits.

FIG. 5 shows a first version of a transmitter coil 50 for application in medical practice. A plate 51 which is suitably shaped to the body is attached to a pivot arm 52, and the transmitter coils and the measuring coils are located inside the plate. The power supply, generator, measuring equipment, control equipment and operating elements are located in a base unit (not illustrated).

Figure 6:
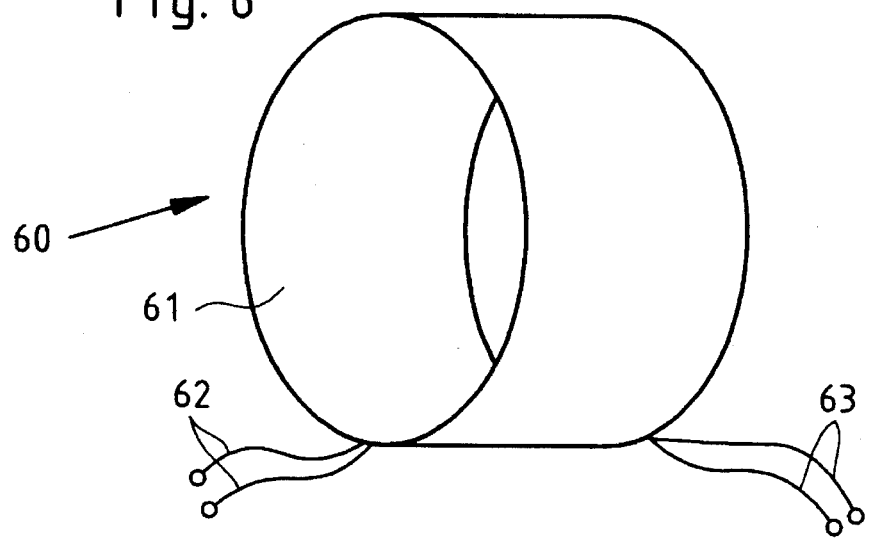

FIG. 6 shows a further embodiment of a transmitter coil 60 which is in this case specially adapted for treating arms and legs, for example, subsequent to breaking a bone. The transmitter coil 60 is in the shape of a cylinder 61 and the power supply leads 62 and measuring leads 63 are connected to it.

Figure 7:
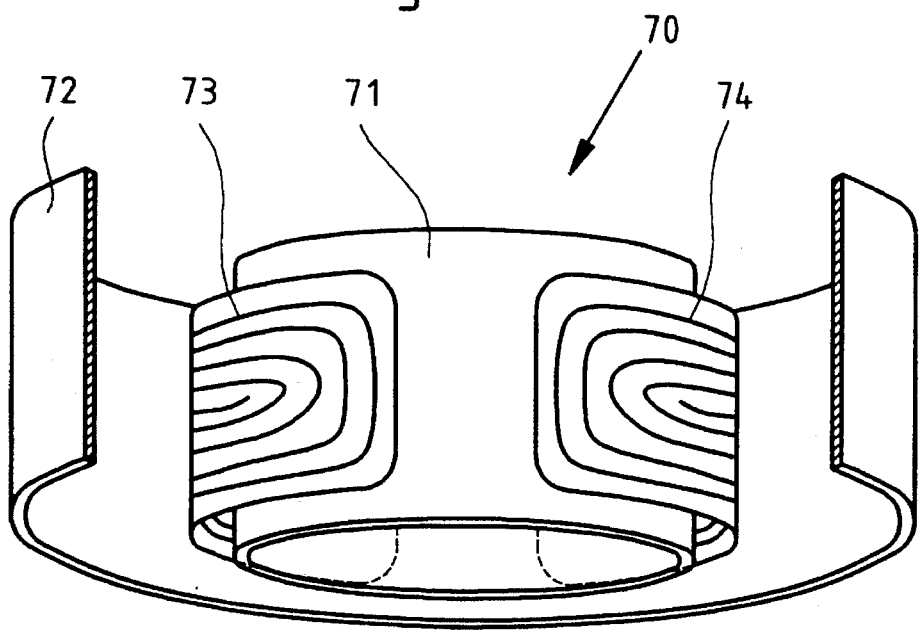

FIG. 7 shows a cylindrical transmitter coil 70 in an exploded view. The actual transmitter coils 73, 74 are located between an inner ring 71 and an outer ring 72, both of which are constructed from insulating material. Both of these transmitter coils are in the form of an oval spiral.

Figure 8:
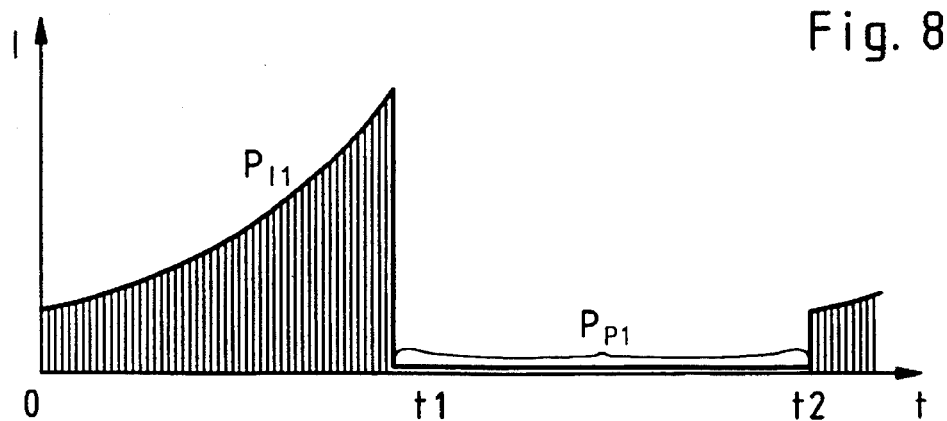

FIG. 8 shows an amplitude/time graph (current I versus time t) illustrating the optimal shape of a basic current pulse $P_{J1}$ followed by a basic pulse interval $P_{P1}$. The duration of a basic current pulse $P_{J1}$ corresponds to the time interval O to $t_1$ and the duration of a basic pulse interval corresponds to the time interval $t_1$ to $t_2$. The pulse/interval ratio is approximately 2:3. The frequency of the basis pulses is between 100 and 1000 Hz, and preferably 200 Hz.

High frequency pulses with a frequency rate between 10 and 100 kHz are superimposed on the basic current pulses $P_{f1}$. The frequency of these high frequency pulses is adjusted to match the capacitive transfer into the vessels of the organism. However, the major feature of the basic current pulse $P_{f1}$ is that its amplitude rises according to an e-function. This curve shape has two important and surprising consequences. On the one hand, the voltage pulses $P_v$ induced in the organism have the same shape, and, on the other hand, they are in phase with the current pulses.

Figure 9:
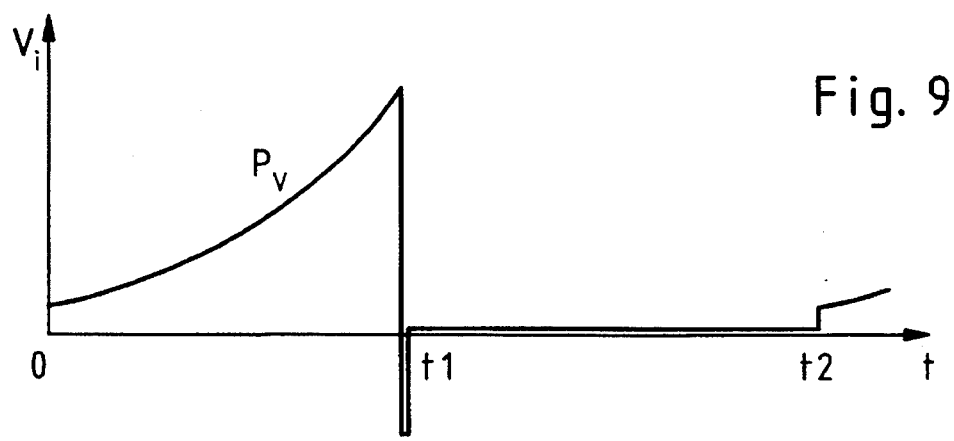

This condition is illustrated in the amplitude/time graph in FIG. 9. The identical shapes of the basic current pulse $P_{f1}$ and the induced voltage pulse $P_v$ is only compromised by a very brief interference pulse at the end of the basic current pulse at time $t_1$. In this graph, the induced voltage $V_i$ is plotted as the parameter on the ordinate.

Thanks to the fact that the current and the voltage are in phase, the energy transmitted into the organism is of the maximum value. Due to the physiological conditions within the organism itself as a result of the blood circulating through long blood vessels, another effect is however also present, namely an effect which involves both positive and negative ions being transported in the same direction. For this reason, it is possible for the first time to supply cells of the organism with both components of a dissociated chemical substance.

Figure 10:
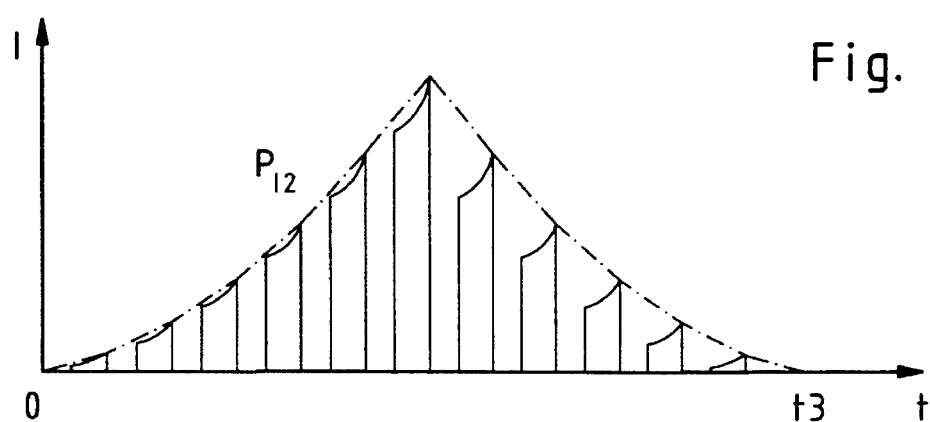

FIG. 10 shows a complete basic pulse sequence $P_{f2}$ using a smaller time scale, whereby the pulse amplitude is modulated using a modulation frequency of 0.5 to 35 Hz, and in a preferred embodiment, of 20 Hz, and whereby the modulation itself approximates to an isosceles triangle without polarity reversal.

Figure 11:
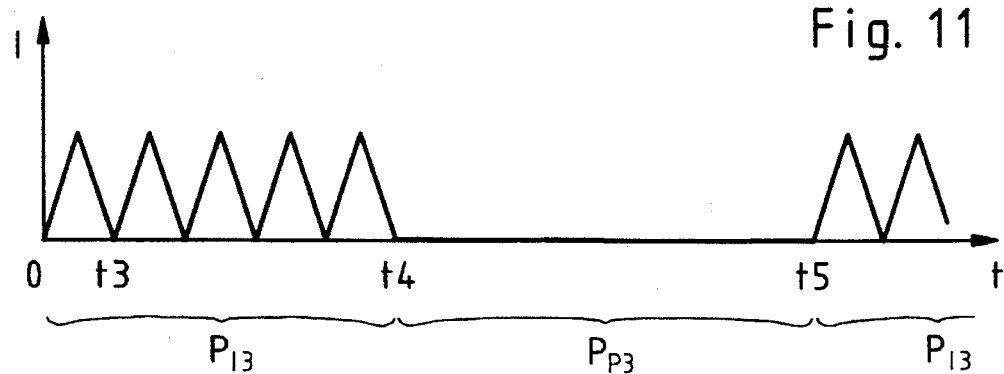

FIG. 11 shows a complete series of pulse sequences $P_{f3}$ using an even smaller time scale whereby the duration of the pulse series corresponds to time O to $t_4$ followed by a pulse series interval $P_{P3}$ with a time duration from $t_4$ to $t_5$. The on/off ratio can be varied between 0.3 to 0.7 sec. The pulse series interval $P_{P3}$ takes account of the fact that the organism always requires a certain amount of time to enable the chemical-physical processes introduced by the pulse sequence series $P_{f3}$ to take effect.

The frequency of the basic current pulses $O_{f1}$ is adjusted to match the mechanical resonance of the blood and lymph vessels. The high frequency is set for the capacitive transfer through the vessel walls and membranes. It is of considerable importance that the pulse amplitude is selected with a sufficient intensity in order to induce the necessary voltages and field intensities in the organism whilst still staying within the correct window. This compliance is monitored using a measuring coil. The electrical conductivity of the irradiated region of the body which is manifested in an increased reflection factor is a measure for improved circulation, while the phase shift between the current and voltage of the measured signal is a measure of the modified polarization of the vessel walls and membranes.

It is to be understood that the physiological effects of the inventive electromagnetic fields can also be monitored using known medical devices for example, a blood pressure gauge, a pulse measuring device, a thermograph, and also a respirograph.

As test have revealed, the configuration and the design of the transmitter coils are especially crucial for an optimal functioning of the inventive device. Although the preferred basic frequency of 200 Hz is extremely low, high frequency harmonic waves arise as a result of the switch-on and switch-off function. If the coil shape is not optimized, these form-determining harmonic waves are not transmitted sufficiently, i.e., the pulse shape is modified and the effect is decreased. For this reason, it is important that the transmitter coils have a low-inductance design. Additionally, the form of the transmitter coils must be such as to prevent any concentrations of field lines which may give rise to detrimental effects in the organism. Since the effect of the magnetic fields is dependent on their direction, the transmitter coils must be applied correctly.

Tests have revealed that, in principle, all biological organisms can be treated. Organisms with well-developed blood or lymph systems such as mammals (including human beings) are prefably treated. With the inventive device it is possible to promote muscle formation and joint regeneration in riding and Jumping horses, increase milk production in dairy cows, and accelerate meat production in pigs. In human treatment, the device can be appropriately used for medicinal and sport applications, especially subsequent to breaking bones.

The following effects on organism have already been verified for electromagnetic fields pulsed in accordance with the present invention due to the effect of the transportation of ions, in particular protons, from the blood into the adjacent tissue and electrolyte spaces, especially in connection with the described effect, namely that both positive and negative ions migrate in the same direction:

As a result of reducing the pH value due to enrichment by protons, the sensitivity of baroreceptors is increased, and this effect is additive to the known mechanical excitation of baroreceptors using electrostriction. Increasing the sensitivity of the baroreceptors reduces excitation of the sympathetic nervous system, promotes vessel dilation, increases measurably heat radiation from the surface of the organism, and raises the partial oxygen pressure in the region of the body to be treated.

Simultaneously to the pH value reduction, the sensitivity of the vagus center is increased, leading to a measurable slowing of the heart beat rate.

A pH value reduction also activates the macrophages.

If the pH value of the liquor is also reduced, the sensitivity of the respiratory center is increased, leading to measurably deeper breathing.

The effect of the pulsed electromagnetic fields is optimal when blood possesses a high proton concentration. This is the case during sleep because the blood contains a high proportion of $CO_2$, following exercise or after consuming alcohol because the lactate concentration in the blood is high, and during fasting because the blood contains a large amount of ketose.

Figure 12:
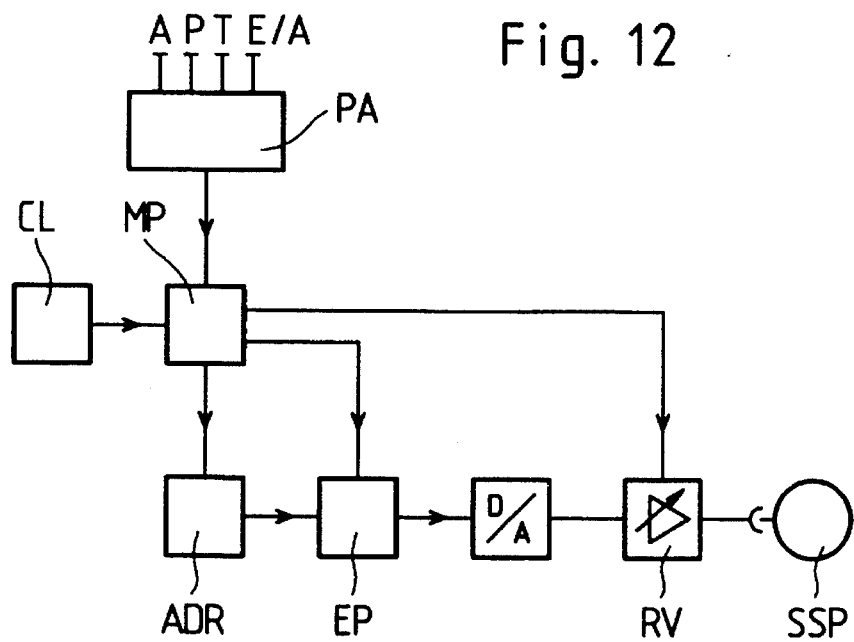
Figure 13:
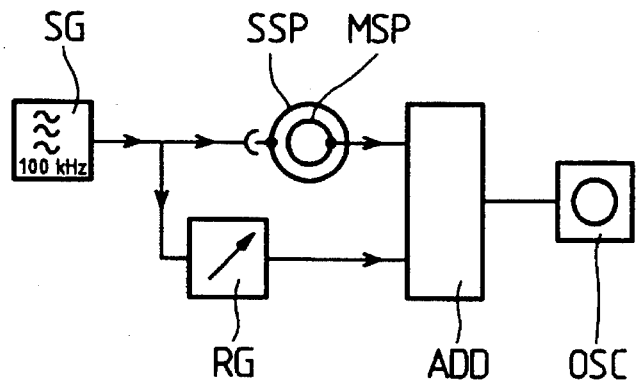
Figure 14:
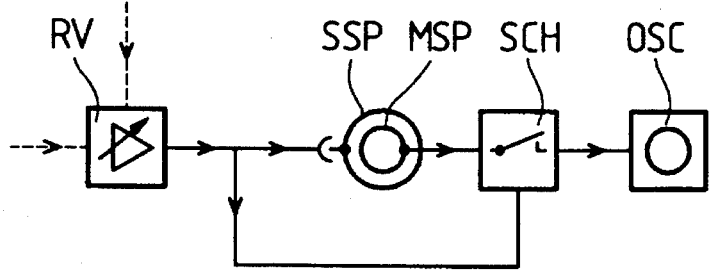

As has already been mentioned, FIGS. 12 to 14 show circuit details of the basic device already discussed using FIG. 5 and of measuring and control devices which have already been referred to.

FIG. 12 shows a block diagram of a tested basic unit. A microprocessor MP is provided in the basic unit in order to control the process sequence, whereby its control parameters are entered using an operating panel PA. The microprocessor MP receives its operating pulse from a pulse signal generator Cl. The required signal form which is to be generated is digitally stored in the form of a sequence of individual amplitude values in a memory chip EP, for example, on EPROM.

A read-out signal is sent to the memory EP by the microprocessor MP, and this signal causes the memory cell contents to be read, whereby the addresses of those cells which are read are specified by the microprocessor MP by means of an address memory and address generator ADR. For this reason, a series of digital values or words is sent out from the output of the memory EP during operation and this series describes the required shape of the transmission signal. This digital signal is converted into a sequence of corresponding amplitude tests using a digital/analog converter A/D, and the amplitude tests are fed to a transmitter coil SSP in the form of a continuous signal through an amplifier RV with lowpass characteristics which has a controllable amplification level.

An adjuster A on the operating panel PA can be used to set the amplification level of the lowpass amplifier RV and therefore the amplitude of the current supplied to the transmitter coil SSP. The sequence of memory cells in the memory EP which are to be read in succession can be specified by using the adjuster P with the microprocessor in order to describe best the required signal shape. The adjuster Z can be used to select the required time values of the pulses which are to be fixed using the microprocessor MP. The operating switch is marked E/A and is used for switching the base unit on and off. This method of generating signals with special shapes is described, for example, in DE-A 3 628 219 so that there in no need for a more detailed description.

FIG. 13 shows a block diagram representation of the aforementioned measuring device switch used for determining the impedance of a region of the body to be treated. A signal generator SG with a frequency of, for example, 11 kHz supplies a transmitter coil SSP which has a measuring coil MSP coordinated therewith. The signal sent to the transmitter coil SSP and the signal taken from the measuring coil MSP are either fed to a subtraction stage when in phase or are sent to an addition stage ADD when out of phase.

Due to the difference in amplitudes between both signals, a control device RG is installed in the line from the signal source to the subtraction or addition stage ADD. The control device RG contains an attenuator in order to compensate the difference in amplitudes and a phase regulator for compensating the phase displacement present in the signal supplied from the measuring coil MSP.

A residual signal appears at the output from the subtraction or addition stage ADD during the measuring process following amplitude and phase compensation, which can be used in conjunction with the value set for phase displacement with the control device RG in order to gain information about the impedance of the region of the body being irradiated by the signal. The phase regulator in the control device RG can be dispensed with if the subtraction or addition phase ADD is provided with a phase comparator in accordance with embodiments of the present invention shown in FIG. 12, whereby the phase comparator measures the phase displacement mentioned above directly and sends the signal to be displayed to a display unit OSC or provides the signal in the form of an adjustment parameter to the operating panel PA or of the microprocessor MP.

FIG. 14 shows a measuring device which is connected to the control amplifier in FIG. 12. The transmitter coil SSP is coordinated with a measuring coil MSP which in turn supplies a measuring device or a display unit such as an oscilloscope OSC. A switch SCH is installed between the measuring coil MSP and the oscilloscope SWC, whereby the switch is supplied by the output signal from the control amplifier RV. In this arrangement, the switch SCH is controlled in such a manner that the transmission path form the measurement coil MSP to the display unit OSC is interrupted for the precise duration of time during which current is sent from the control amplifier RV to the transmitter coil SSP, in other words, whenever pulses are being emitted. During the pulse intervals, i.e., when RV is not supplying current to SSP, that transmission path is blocked. The signal picked up by the measurement coil MSP during the pulse interval therefore passes through to the display unit, which in the embodiment shown is an oscilloscope OSC.

The circuit shown in FIG. 13 can also be used for a similar purpose if the control amplifier RV in accordance with FIGS. 12 or 14 replaces, or is connected in the circuit instead of, the 100 kHz generator SG.

The measurement signal obtained using circuits in accordance with FIGS. 13 and 14 can be used in two ways for controlling the transmitter currents. One possibility is that the measurement signal can be displayed and the operator can move the adjusters on the operating panel accordingly. The other possibility is that the measuring signals can be used directly as adjustment parameters for the control amplifier RV or for the microprocessor MP by having them undertake a corresponding modification to the amplification and/or alteration to the pulse shape, or by using them to change the time control to an appropriate degree.

The present invention is, of course, in no way restricted to the specific disclosure of the specification and drawings, but also encompasses any modifications within the scope of the appended claims.

What we claim is:

1. A device comprising:

a generator for generating low-frequency pulsed electric currents;

a transmitter coil connected to said generator for applying electromagnetic fields to a body region of a living organism;

said device designed for transporting ions from intracorporal electrolyte liquids of the living organism into and through surrounding vessel walls and membranes such that a transmitting energy is selected to such a high value that the energy induced within said electrolyte liquid is greater than a thermal energy and is within a cell-specific amplitude window; and wherein pulsed currents generated within said transmitter coil by said generator have the following properties:
  a) a basic current pulse of a first duration consists of a square current and a superimposed current increasing according to an exponential function;
  b) a pulse interval subsequent to said basic current pulse having a second duration that is at least equal to said first duration;
  c) a basic frequency of said basic current pulse with said pulse interval is 100 to 1000 Hz;
  d) an amplitude of a sequence of said basic current pulses is modulated with a modulation frequency of 0.5 to 35 Hz to yield a modulation amplitude;
  e) said sequence of said basic current pulse is emitted as a series for a period of 0.3 to 1.0 sec; and
  f) said series is followed by a series interval of 0.7 to 5.0 sec.

2. A device according to claim 1, wherein said basic frequency is 200 Hz.

3. A device according to claim 1, wherein said modulation frequency is 20 Hz.

4. A device according to claim 1, wherein a ratio of said first duration to said second duration is 2:3.

5. A device according to claim 1, wherein high frequency pulses of a 10 to 100 kHz are superimposed over each said basic current pulse.

6. A device according to claim 1, wherein said modulation amplitude forms an isosceles triangle.

7. A device according to claim 1, wherein said sequence of said basic current pulses is modulated without a polarity reversal.

8. A device according to claim 1, said device further comprising at least one measuring coil, wherein during said series interval a sinusoidal measuring current of a frequency in a range of 100 kHz is supplied to said transmitter coil, and wherein a measured signal of said measuring coil is used for determining an electric impedance and electric polarization of the body region being irradiated.

9. A device according to claim 1, wherein said generator has means for adjusting field parameters including frequency, amplitude, curve shape, and on- and off-times, and wherein said generator further comprises a bio-feedback control system for adjusting optimally said parameters.

10. A device according to claim 9, wherein said biofeedback control system comprises at least one measuring coil.

11. A device according to claim 10, further comprising an evaluation circuit connected to said measuring coil, said evaluation circuit further comprising a regulator, wherein an evaluated signal of said evaluation circuit is used to optimize the parameters of the transmitter coil pulses via said regulator.

12. A device according to claim 10, wherein said measuring coil is circular and has a diameter of 20 cm, and wherein said transmitting energy is selected to such a value that said magnetic field reflected by the living organism generates in said measuring coil a measuring voltage of 20 to 30 mV.

13. A device according to claim 10, further including means for supplying during said series interval a sinusoidal measuring current of a frequency in a range of 100 kHz to said transmitter coil, and means for determining, based on a measured signal of said measuring coil, an electric impedance and electric polarization of the body region being irradiated.

14. A device according to claim 10, wherein a plurality of said measuring coils are provided that are switchable, wherein each said measuring coil has dimensions adapted to a body region to be treated.

15. A device according to claim 10, wherein said at least one measuring coil measures a magnetic field reflected by the living organism being irradiated.

16. A device according to claim 10, further comprising a carrier plate to which said transmitter coil is connected, wherein said measuring coil is wrapped around said transmitter coil.

17. A device according to claim 10, wherein three said measuring coils are provided that are switchable, wherein each said measuring coil has a diameter adapted to a body region to be treated.

18. A device according to claim 9, wherein said biofeedback control system comprises a blood pressure measuring device for determining control parameters.

19. A device according to claim 9, wherein said biofeedback control system comprises a thermograph for determining control parameters.

20. A device according to claim 9, wherein said biofeedback control system comprises a pulse measuring device for determining control parameters.

21. A device according to claim 9, wherein said biofeedback control system comprises a breathing volume measuring device for determining control parameters.

22. A device according to claim 1, wherein said transmitter coil includes means for preventing local field peaks of the field emitted onto the living organism.

23. A device according to claim 22, wherein windings of said transmitter coil are forming a quadrupole.

24. A device according to claim 22, wherein said transmitter coil is an oval spiral.

25. A device according to claim 24, further comprising a carrier plate to which said transmitter coil is connected, wherein loops of said transmitter coil are distributed on both sides of said carrier plate.

* * * * *